United States Patent [19]

Uzgiris

[11] 4,102,990
[45] Jul. 25, 1978

[54] ELECTROPHORETIC ASSAY FOR ANTIGEN-ANTIBODY REACTION BASED ON PARTICLE-PARTICLE COUPLING

[75] Inventor: Egidijus E. Uzgiris, Schenectady, N.Y.

[73] Assignee: General Electric Company, Schenectady, N.Y.

[21] Appl. No.: 857,420

[22] Filed: Dec. 5, 1977

[51] Int. Cl.² ..................... G01N 27/26; G01N 33/16
[52] U.S. Cl. ..................................... 424/12; 23/230 B; 23/253 R; 204/299 R; 204/DIG. 11; 424/8; 424/11; 424/13
[58] Field of Search ......................... 424/8, 11, 12, 13; 23/230 B; 204/DIG. 11, 299

[56] References Cited

U.S. PATENT DOCUMENTS

| 3,975,238 | 8/1976 | Bean | 23/230 B X |
| 3,984,533 | 10/1976 | Uzgiris | 424/12 |
| 4,011,044 | 3/1977 | Uzgiris | 424/12 X |

*Primary Examiner*—Albert T. Meyers
*Assistant Examiner*—A. P. Fagelson
*Attorney, Agent, or Firm*—Nathan D. Herkamp; Joseph T. Cohen; Leo I. MaLossi

[57] ABSTRACT

Polystyrene particles having attached antigen and high electrophoretic mobility, and polystyrene particles having attached antigen and low electrophoretic mobility, when paired in a common solution with antibodies specific to the antigen, give rise to a particle population of intermediate electrophoretic mobility when measured by the Doppler shift of scattered laser light, thereby signaling presence of the antibodies in the solution.

8 Claims, 1 Drawing Figure

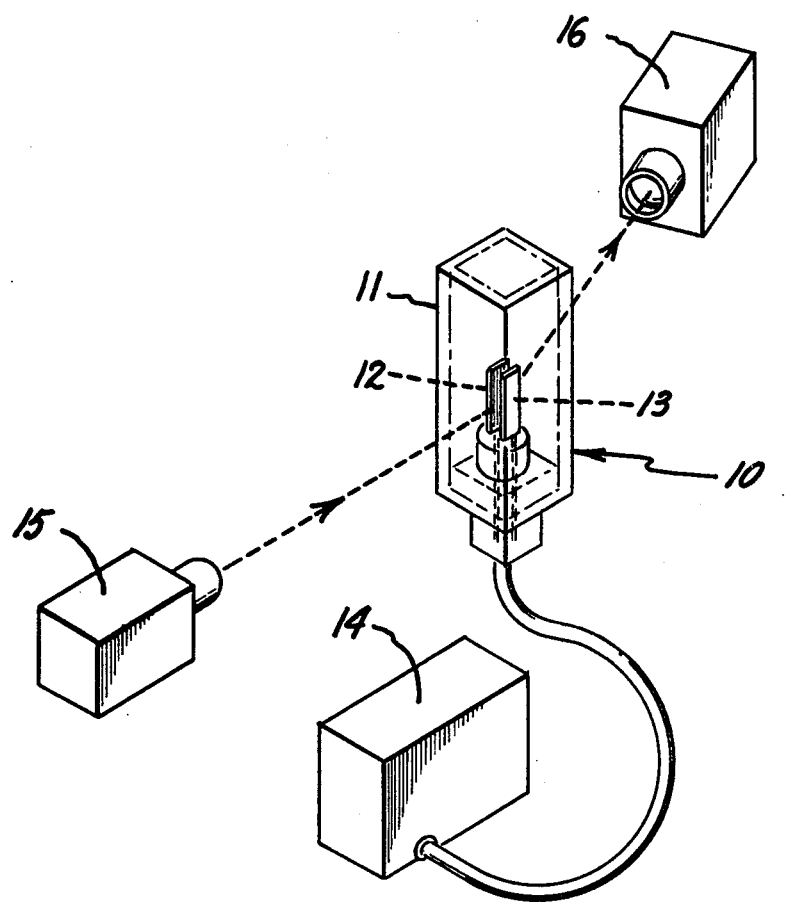

ELECTROPHORETIC ASSAY FOR ANTIGEN-ANTIBODY REACTION BASED ON PARTICLE-PARTICLE COUPLING

INTRODUCTION

This invention relates to detection of proteins, and more particularly to a method of rapidly detecting presence of specific antibodies in a solution.

In E. E. Uzgiris U.S. Pat. No. 3,984,533, issued Oct. 5, 1976 and assigned to the instant assignee, an electrophoretic method of detecting an antigen-antibody reaction is described and claimed. The method generally comprises the steps of depositing an antigen on each of a plurality of microscopic particles, and forming a dilute suspension of the particles in a solution to be tested for presence of antibodies specific to the antigens on the particles. After the suspension is stirred, reduction in electrophoretic mobility of the particles, indicated by detecting a Doppler shift in frequency of laser light which is scattered by the particles, signifies that an antigen-antibody reaction has taken place.

In E. E. Uzgiris et al. application Ser. No. 842,952, filed Oct. 17, 1977 and assigned to the instant assignee, a resistive pulse method of detecting an antigen-antibody reaction is described and claimed. This method generally comprises the steps of preparing first and second suspensions of particles of first and second predetermined sizes, respectively, each particle of both suspensions being coated with a layer of a first protein. The second predetermined size is preferably between 1 and 2 times the volume of the first predetermined size. The first and second suspensions are then combined into a solution which is to be tested for presence of a second protein specific to the first protein by using a resistive pulse technique to detect multiplets of particles formed by aggregation of a particle of the first predetermined size with a particle of the second predetermined size.

Both the electrokinetic measurement method of the aforementioned Uzigiris patent and the particle aggregation measurement method of the aforementioned Uzgiris et al. application constitute very sensitive techniques for probing antigen-antibody reactions. Those skilled in the art will appreciate, however, the necessity for employing a particle of high mobility and for providing large fractional coverage of the particle surface with antigen, when implementing the method of the aforementioned Uzgiris patent. This condition precludes use of antigen-coated particles with low electrophoretic mobility in making these electrokinetic measurements, and also results in relatively high susceptibility of the particle to nonspecific effects. If the antigen coverage of the particle surface were low, the signal associated with antibody attachment would be small and sensitivity of the assay would be low.

Rather than using a single type of protein bonded to a microscopic particle, as in the case of the afore-mentioned Uzgiris patent and Uzgiris et al. application, the present invention contemplates using two types of antigen-coated particles to assay for antibodies in solution. Antigen is bonded covalently to carboxylated polystyrene latex spheres of high electrical charge and high electrophoretic mobility, and to carboxylated polystyrene latex spheres of low electrical charge and low electrophoretic mobility. Complete coverage of the latex particle surface is not required, so that an antigen-coated particle of high or low electrophoretic mobility can be produced. This is in contrast to the method described and claimed in the aforementioned Uzgiris U.S. Pat. No. 3,984,533 wherein particle mobility is fixed by the properties of the antigen molecule since full particle surface coverage is required in that procedure.

In the present invention, the two types of antigen-coated particles suffer small electrophoretic mobility decreases, depending upon the number of antigenic sites per particle, as antibodies become attached to the antigenic sites. However, particle-particle pairing by antibody molecules gives rise to a particle electrophoretic mobility population intermediate the high and low electrophoretic mobility values. The population of these intermedial electrophoretic mobility particles in the suspension under study constitutes a signal for the presence of antibody.

Accordingly, one object of the invention is to provide a sensitive assay for an antigen-antibody reaction.

Another object is to provide an assay for an antigen-antibody reaction employing antigen-coated microscopic particles of low electrophoretic mobility together with antigen-coated microscopic particles of high electrophoretic mobility.

Another object is to provide an assay for an antigen-antibody reaction which does not require that antigenic coating of each microscopic latex sphere be accomplished over substantially the entire surface area of the sphere.

Briefly, in accordance with a preferred embodiment of the invention, a method of detecting an antigen-antibody reaction comprises preparing a first suspension of particles of high electrophoretic mobility with a type of antigenic molecules bonded thereto, and preparing a second suspension of particles of low electrophoretic mobility with the same type of antigenic molecules bonded thereto. The particles in each of the first and second suspensions are washed, and the first and second suspensions are mixed in a solution to be tested for antibodies specific to the antigenic molecules on the particles. Electrophoretic mobilities of particles intermediate the aforesaid high and low electrophoretic mobilities are then detected as an indication that an antigen-antibody reaction has occurred.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings in which:

The single FIGURE is an isometric view of apparatus that may be employed in practicing the method of this invention.

DESCRIPTION OF TYPICAL EMBODIMENTS

In preparing antigenic-coated particles of both high and low electrophoretic mobilities, carboxylated polystyrene latex spheres of 0.86 micrometers mean diameter, for example, available from Dow Chemical Company, Indianapolis, Indiana, are bound to antigenic protein by covalent bonding methods. These latex spheres are of relatively high charge and therefore capable of exhibiting relatively high electrophoretic mobilities. In the alternative, cross-linked latex spheres of methacrylate derivatives, such as described by R. S. Molday et al., "New Immunolatex Spheres: Visual Markers of Antigens on Lymphocytes For Scanning Electron Microscopy", *Journal of Cell Biology*, 64, (1975), pages 75–88, may be covalently bonded to antigenic protein. In each instance, the covalent bond may be achieved by well known methods such as the carbodiimide method, the glutaraldehyde method, or the cyanogen bromide method, each as described in the aforementioned Molday et al. article.

One way of producing antigen-coated spheres with low electrophoretic mobilities (i.e., low electric charge or zeta potential) is to cover the spheres with immunoglobulin molecules through physical adsorption on polystyrene; however, for purposes of the present invention this is preferably accomplished by covalent coupling methods as described in the Molday et al. article. The spheres (also known as beads) may then be exposed to polymeric molecules such as polyethyleneamine, which are positively charged, to neutralize most of the negative charge groups on the beads. The number of charge groups resulting from the initial step of making the beads may be reduced, if necessary, by altering the polymerization condition; that is, by reducing the nominal concentration of methacrylic acid in the polymerization conditions described by Molday et al.

Antigenic-coated spheres with high electrophoretic mobilities (i.e., high electric charge or zeta potential) may be prepared by covering the beads with albumin molecules through physical adsorption, in the manner set forth by E. E. Uzgiris, "A Laser Doppler Assay for the Antigen-Antibody Reaction", *Journal of Immunological Methods*, 10, (1976) pages 85–96; however, for purposes of the present invention this is preferably accomplished through covalent bonding methods. The number of charge groups resulting from the initial step of making the beads may be increased, if necessary, by altering the polymerization conditions; that is, by increasing the nominal concentration of methacrylic acid in the polymerization conditions described by Molday et al.

Preparation of specifically labeled beads of high or low charge is accomplished by leaving a small numberof sites on the bead surface for the antibody or antigen. If, for example, in the low charge case, a specific antibody is mixed together with the nonspecific immunoglobulin molecules, after covalent bonding the fractional concentrations in solution would determine the fractional coverage of the particle surface. The specificity is determined by the small fraction of the surface covered with specific antibody or specific antigen, while the charge is determined by the large scale coverage of high charge molecules such as albumin or low charge molecules such as immunoglobulins.

The test spheres are washed free of excess protein solutions either during preparation of the spheres or just before their exposure to serum. The washing can be performed by spinning for ten minutes at 2500 g. For adsorption of antigen, for example, to spheres, the spinning may be performed three times, finally suspending the spheres in sodium chloride solution, conveniently 0.005 Normal. In testing for antigen-coated particle interaction with antibodies, the particles may be washed free of excess serum by spinning for five minutes at 5,000 g three times. In each instance, the spinning may be performed in a centrifuge, such as a Fisher Model 59.

The antigen-coated particles of high electrophoretic mobility and the antigen-coated particles of small electrophoretic mobility each undergo small mobility decreases, depending upon the number of antigenic sites per particle, as antibodies become attached to the antigenic sites. However, particle-to-particle pairing by antibody molecules bound to antigenic sites on the spheres in the solution gives rise to a particle mobility population tht is intermediate the high and low electrophoretic mobilities of the antigen-coated particles; that is, the zeta potential averaged over the particle surface of the paired particles is intermediate to the individual particle zeta potential averages. Detection of this intermedial particle mobility population in the suspension indicates presence of antibodies specific to the antigen on the particles.

The electrophoretic mobilities may be measured by detecting laser light that is scattered by the particles. The scattered light exhibits a shift in frequency as an electric field is applied to the particle solution, due to the Doppler effect and electrophoretic motion of the particles. This type of measurement, which is described by E. E. Uzgiris in "Electrophoresis of Particles and Biological Cells Measured by the Doppler Shift of Scattered Laser Light", *Optics Communications*, 6 (September, 1972) 55, allows fractional coverage of the particle surface with antibody molecules to be readily observed.

An optical Doppler electrophoresis measurement system for detecting mobility changes, such as described in the aforementioned Uzgiris *Optics Communications* article and also illustrated in E. E. Uzgiris U.S. Pat. No. 3,984,533, issued Oct. 5, 1976 and assigned to the instant assignee, is illustrated in the FIGURE. The system comprises an electrophoretic cell 10 including fluid containment means 11 fabricated of a light-transmissive, fluid-impenetrable material, such as glass, plastic or the like. A pair of closely-spaced electrodes 12 and 13 are included in cell 10. These electrodes are preferably of rectangular shape and have mutually-parallel facing surfaces defining an interelectrode gap not exceeding one millimeter in width.

Container 11 is filled with a dilute colloidal suspension to be tested for presence of antibodies, the suspension containing the microscopic particles having a layer of protein bonded thereto. An electric field is established between electrodes 12 and 13 by power supply 14, and the gap between the electrodes is illuminated by coherent optical energy from a laser 15. A portion of this energy is scattered by the microscopic particles within the gap between electrodes 12 and 13 and, because of the motion of the scattering particles in the electric field, exhibits a Doppler frequency shift. Energy scattered at a predetermined angle is received by optical detector 16 which is preferably a photomultiplier tube but may be any appropriate square law detector.

Detector 16 receives the Doppler-shifted energy scattered by the particles in suspension in the fluid inside container 11, and also receives unshifted energy scattered by fixed scattering objects, such as a wall of container 11. Since detector 16 receives both Doppler-shifted and unshifted energy, and is a square law detector, its output signal is indicative of the heterodyne product of the two frequencies received and hence may be analyzed by conventional techniques to determine electrophoretic mobility of the particles in cell 10. This determination may be made by measuring mobilities of the particles of high charge and the particles of low charge separately, and then measuring mobility of the particles in the dilute colloidal suspension to be tested for presence of antibodies in order to detect a mobility that is intermediate the mobilities of the particles of high charge and the particles of low charge. Due to the high sensitivity of this technique, a small, developing, intermediate mobility population of particles is likely to be detected in the presence of the two starting populations of particles.

The technique described herein requires only a few antigenic sites per particle, and the approach is workable for any antigen-antibody system. Use of covalent bonding methods makes it possible to minimize nonspecific effects and also makes it possible to look for antigen in solution directly without need for the inhibition methods presently in use in clinical practice and which are fundamentally limited by the finite value of the equilibrium constant of the antigen-antibody reaction.

The foregoing describes a sensitive assay for an antigen-antibody reaction employing antigen-coated microscopic particles of low electrophoretic mobility together with antigen-coated microscopic particles of high electrophoretic mobility. The assay does not require that antigenic coating of each microscopic latex sphere be accomplished over substantially the entire surface area of the sphere. Moreover, those skilled in the art will appreciate that, while the foregoing description concerns detection of antibodies by employing antigen-coated particles, the invention is equally applicable to detection of antigens by employing antibody-coated microscopic latex spheres; that is, either antigenic protein may be employed for detecting antibody protein, or antibody protein may be employed for detecting antigenic protein.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

I claim:

1. A method of detecting a reaction between antigenic protein molecules and antibody protein molecules, comprising:
   preparing a first suspension of particles of high electrophoretic mobility with a first type of said protein molecules bonded thereto;
   preparing a second suspension of particles of low electrophoretic mobility with said first type of protein molecules bonded thereto;
   forming a mixture of said first and second suspensions in a solution to be tested for a second type of protein specific to said first type of protein on said particles; and
   detecting electrophoretic mobility of particles intermediate said high and low electrophoretic mobilities as an indication that an antigen-antibody reaction has occurred.

2. The method of claim 1 including the step of washing the particles in each of said first and second suspensions.

3. The method of claim 1 wherein said first type of protein comprises an antigen and said second type of protein comprises an antibody.

4. The method of claim 1 wherein said first type of protein comprises an antibody and said second type of protein comprises an antigen.

5. The method of claim 1 wherein the step of detecting electrophoretic mobility of particles intermediate said high and low electrophoretic mobilities comprises the steps of:
   measuring electrophoretic mobility of particles in said mixture originating from said first suspension of particles;
   measuring electrophoretic mobility of particles in said mixture originating from said second suspension of particles; and
   measuring electrophoretic mobility of particles in said mixture intermediate said high and low electrophoretic mobilities at a predetermined time after said mixture has been formed.

6. The method of claim 5 including the step of washing said particles in each of said first and second suspensions.

7. The method of claim 5 wherein said first type of protein comprises antigens and said second type of protein comprises antibodies.

8. The method of claim 5 wherein said first type of protein comprises antibodies and said second type of protein comprises antigens.

* * * * *